United States Patent [19]

Dixon et al.

[11] 4,111,877
[45] Sep. 5, 1978

[54] ALLYL ESTERS OF N-ALKYL-OMEGA-(ALKYLENEUREIDO) AMIC ACIDS AND THEIR SYNTHESIS AND USE IN AQUEOUS EMULSION POLYMER SYSTEMS

[75] Inventors: Dale D. Dixon, Kutztown; Frederick L. Herman, Allentown, both of Pa.

[73] Assignee: Air Products & Chemicals, Inc., Allentown, Pa.

[21] Appl. No.: 709,677

[22] Filed: Jul. 29, 1976

[51] Int. Cl.$^2$ .............................................. C08L 39/04
[52] U.S. Cl. ........................... 260/29.6 R; 260/29.6 T; 528/320; 544/267
[58] Field of Search ..................... 260/29.6 R, 29.6 T, 260/256.4 C; 528/320

[56] References Cited

U.S. PATENT DOCUMENTS

| | | | |
|---|---|---|---|
| 2,831,833 | 4/1958 | Aycock et al. | 548/320 |
| 2,881,155 | 8/1959 | Hankins | 548/320 |
| 3,973,946 | 8/1976 | Wat | 260/256.4 C |

*Primary Examiner*—M. J. Welsh
*Attorney, Agent, or Firm*—William F. Marsh; Barry Moyerman

[57] ABSTRACT

Novel compounds of the general formula

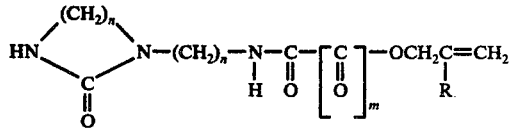

($m = 0$ or 1; $n = 2$ or 3 and R = H or CH$_3$)

are produced by reacting a 2-aminoalkyl alkylene urea with an allyl ester of a carbonylic acid. Among the particular allyl esters disclosed as reactants are diallyl carbonate, allyl and methallyl chloroformate, diallyl and dimethallyl oxalate. The recovered allyl esters of the alkyleneureido amic acid compounds find particular use as functional comonomers for imparting wet adhesion properties to emulsion systems containing vinyl ester polymers used in paints and coating compositions.

20 Claims, No Drawings

ALLYL ESTERS OF N-ALKYL-OMEGA-(ALKYLENEUREIDO) AMIC ACIDS AND THEIR SYNTHESIS AND USE IN AQUEOUS EMULSION POLYMER SYSTEMS

BACKGROUND OF THE INVENTION

1. Field of the Invention

This invention relates generally to new N-cyclic ureido alkylamino derivatives, wherein the amino nitrogen is attached by a carbonyl-containing chain to a terminal ethylenically unsaturated group. More particularly, the invention is concerned with the preparation of novel compounds of the general formula

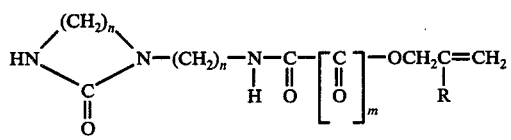

where $m$ is 0 or 1, $n$ is 2 or 3 and R is H or $CH_3$. These compounds can be regarded respectively as N-aminoalkyl derivatives of imidazolidinone when $n$ is two and as N-aminoalkyl derivatives of tetrahydropyrimidinone when $n$ is 3. These compounds are particularly useful, among other purposes, as functional monomers for imparting excellent wet adhesion properties to water-based paints and coating compositions comprising vinyl ester emulsions.

2. Prior Art

The prior art discloses a wide variety of unsaturated derivatives of N-(omega-aminoalkyl) cyclic ureides capable of undergoing condensation and polymerization reactions. Certain of such compounds are indicated, among other suggested uses, as additives to paper sizing and coating formulations for improving wet strength, as anti-static additives, and as components of water-based paints and coatings to improve freeze-thaw stability, and adhesion to various substrates, including weathered and chalky surfaces or glossy oil-painted surfaces. Typical examples of these prior art disclosures and of the various types of compounds suggested are found in U.S. Pat. No. 2,881,155; 2,980,652; 3,194,792; 3,280,034; 3,300,429; 3,369,008; and 3,509,085.

The compounds of the present invention differ from those heretofore disclosed in the prior art, in a number of important respects, as will hereinafter appear.

SUMMARY OF THE INVENTION

It has now been found that allyl esters of N-alkyl-omega-alkyleneureido amic acid compounds can be prepared in good yield and ddesired purity by methods hereinafter described. These compounds, in contrast to the known cyclic ureido derivatives of the prior art, are characterized by the presence in the carbonyl-containing chain, attached to the amino nitrogen of the aminoalkyl ureide, of a terminal ethylene group not directly attached to carbonyl carbon. These novel compounds are prepared by reaction of an allyl or methallyl ester of a carbonylic acid with (a) N-$\beta$-aminoethyl ethyleneurea to produce compounds of the structure

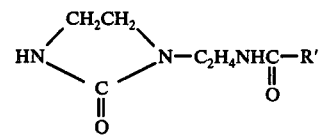

or with (b) N-gamma aminopropyl propyleneurea to produce compounds having the structure

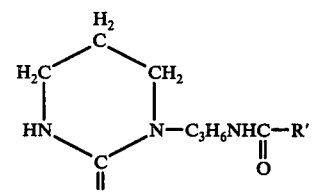

wherein R″ (in each case) is either

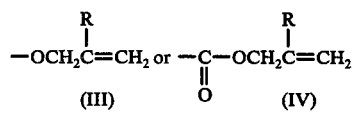

wherein R is as above defined. As used herein, the term "carbonylic acid" includes carbonic acid and carboxylic acids. Compounds containing an R′ group corresponding to III above are obtained by reacting the N-aminoalkyl alkylene urea with diallyl carbonate or with allyl or methallyl chloroformate. Compounds containing an R′ group corresponding to IV above are obtained by reacting the N-aminoalkyl alkylene urea with diallyl or dimethallyl oxalate.

Incorporation of the novel compounds of the invention at levels of approximately 2% into otherwise water-sensitive vinyl acetate based emulsions enables the production of water resistant films which pass the standard cut film scrub test at 5000 cycles and also possess excellent peel adhesion when applied to alkyd coated surfaces or other glossy or semiglossy painted surfaces.

DESCRIPTION OF PREFERRED EMBODIMENTS

The starting material for preparation of the novel compounds corresponding to formula I above is 2-aminoethyl ethylene urea, corresponding to the formula

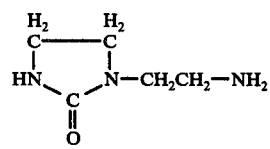

which compound is available commercially or it can be prepared by methods described in U.S. Pat. No. 2,613,212. Thus, this compound can be synthesized by the reaction of diethylenetriamine with urea.

Production of Allyl N-ethyl-β-(1-ethyleneureido) Oxamate

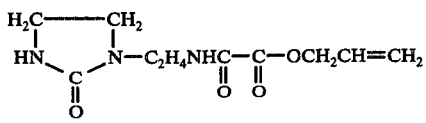

(VI)

The diallyl oxalate intermediate may be prepared by the method described in Bulletin Societe Chimique France (1960) page 110.

EXAMPLE 1

307 parts by weight of 2-aminoethyl ethylene urea (V) was added dropwise over a one hour period to 404 parts of diallyl oxalate dissolved in 147 parts acetone. The solution was stirred for 72 hours at room temperature, filtered, and the solvent evaporated, leaving an oil. 452 parts of the desired product (VI) were obtained (yield 79%). Analysis showed:

|  | C | H | N |
|---|---|---|---|
| Theory | 49.81 | 6.22 | 17.43 |
| Found | 49.43 | 6.40 | 17.38 |

While in the foregoing example the components were reacted in 1:1 molar ratio, which is preferred, higher proportions of diallyl oxalate may be employed in the range of 1 to 10 mols of the oxalate per mol or urea compound. Instead of acetone, other organic solvents for diallyl oxalate may be used, including: dimethylformamide, acetonitrile, methanol, ethanol, dimethoxyethane, diethyl ether, tetrahydrofuran, benzene, chloroform, dichloromethane, carbon tetrachloride, dioxane, etc. If desired, the reaction may be carried out in the absence of solvent. The reaction temperature is not critical and may be in the range of −20° to 150° C, preferably about room temperature (25° C).

EXAMPLE 2

Production of Allyl N-ethyl-β-(1-ethyleneureido) carbamate

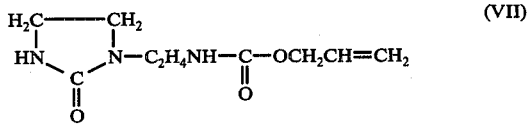

(VII)

302 parts by weight of 2-aminoethyl ethyleneurea were admixed with 336 parts of diallyl carbonate, and the mixture stirred for 15 hours at 110° C. The allyl alcohol formed was driven off by evaporation. By recrystallization of the residual reaction product from ethyl acetate, 233 parts of a crystalline product was obtained (46% yield) having a melting point of 57°–59° C. Analysis showed:

|  | C | H | N |
|---|---|---|---|
| Theory | 50.72 | 19.72 | 7.03 |
| Found | 50.71 | 20.08 | 7.19 |

The intermediate diallyl carbonate may be prepared by the methods described in U.S. Pat. No. 2,648,697. For example, allyl chloride is reacted with sodium carbonate in the presence of a catalytic quantity of triethylamine, at 125° C.

In the foregoing example (2) substantially equimolar quantities of diallyl carbonate and aminoethyl ethyleneurea were employed. In general, the molar ratio of the reactants may be in the range of 1 to 5 mols of diallyl carbonate per mol of the urea compound, with the ratio of about 1:1 being preferred. Inert solvents may be used in the reaction, if desired. The temperature range for the reaction is 10° to 150° C, preferably 80° to 120° C.

EXAMPLE 3

The carbamate compound of Example 2 (VII) may also be prepared using allyl chloroformate instead of diallyl carbonate.

27.5 grams of allyl chloroformate in 50 ml dichloromethane was added dropwise over a 1 hour period into a stirred suspension of 29.5 grams of 2-aminoethyl ethyleneurea in 50 ml dichloromethane and 29 ml aqueous sodium hydroxide (40% w/v). The reaction temperature was maintained at 5°–12° C by an external ice bath during the addition. Then the solution was stirred at room temperature for an additional ¾ hour. The organic layer was separated and the aqueous layer washed with dichloromethane. The combined organic phase was dried with magnesium sulfate, filtered and evaporated, obtaining 45.5 grams (94% yield) of a crystalline material having properties similar to the product obtained in Example 2.

In general, the method of Example 3 may be carried out at molar ratios of 2-aminoethyl ethyleneurea: allyl chloroformate ranging from 1:1 to 1:5; approximately equimolar ratios being preferred. The molar ratio of allyl chloroformate to sodium hydroxide may range from 1:1 to 1:5 but it is preferred to operate within the range 1:1 and 1:1.5. The reaction temperature may be in the range from −10° to +90° C, preferably in the range of 15° to 35° C. Instead of the preferred dichloromethane, other solvents can be employed, such as hydrocarbons, halohydrocarbons or ethers.

The allyl chloroformate used as reactant may be prepared by methods described in U.S. Pat. No. 2,384,115. For example, by reaction of equimolar proportions of phosgene with allyl alcohol at room temperature.

The novel monomers of the invention can be introduced into aqueous paint or coating formulations by interpolymerization in emulsions comprising vinyl ester systems which may also contain one or more other unsaturated monomers. Thus, such systems may comprise vinyl acetate along or in admixture with one or more alkyl esters of acrylic, methacrylic, and/or maleic acid or with ethylene. Such emulsion systems generally comprise, in addition to the polymerizable monomer or monomers, free radical initiators and emulsifying, stabilizing, and surface active agents. Preferably, the activator comprises a redox system, typically made up of a peroxide or persulfate catalyst and a reducing component, such as an alkali metal formaldehyde bisulfite. The principal emulsifying agent is preferably of the nonionic type, for example, one or more alkyl phenoxy poly (oxyethylene) ethanols. The formulation may also include surface active agents of the anionic type and suitable buffering agents.

EXAMPLE 4

Two similar aqueous paint compositions were prepared comprising as monomers in the emulsion, 97 parts of vinyl acetate to about 1 part maleic acid. To one of these compositions there was added about 2 parts of a compound corresponding to formula VII. To each of the emulsion compositions, a pigment dispersion was added and the obtained paints tested by a slightly modified version of the standard procedure outlined in the Federal Specification TT-P-001511, paragraph 4.3.9 to determine adhesion properties. The paint composition containing the compound of formula VII passed 5000 cycles in the scrub test while the other composition failed by loss of adhesion between it and the alkyd undercoat in less than 100 cycles.

The emulsion employed in the aqueous paint compositions tested was prepared as follows. The jacketed reaction vessel initially was charged with:

|  | pbw |
|---|---|
| Sodium vinyl sulfonate (25%) | 2.4 |
| Sodium vinyl sulfonate polymer (25%) | 3.0 |
| *Maprofix | 3.2 |
| Alkyl phenoxy poly (oxyethylene) ethanols | 43.6 |
| Citric acid | 5.7 |
| Sodium acid phosphate | 5.1 |
| Potassium persulfate | 3.0 |
| Ferrous salt | (trace) |
| Vinyl acetate | 75.0 |
| De-ionized water | 450.0 |

*Maprofix is an anionic emulsifying agent comprising sodium borosulfates of higher fatty alcohols.

The mixture was purged with nitrogen while heating to 50° C with stirring. There was then added an activator solution consisting of 2 parts sodium formaldehyde bisulfite in 198 parts de-ionized water. Then over a 3 hour period, there was added to the vessel after reaction was initiated.

|  | pbw |
|---|---|
| Vinyl acetate | 628.0 |
| Maleic anhydride | 7.5 |
| Compound of formula VII | 15.0 |
| Sodium vinyl sulfonate (25%) | 3.0 |
| De-ionized water | 400.0 |

The reaction temperature was maintained at about 50° C. The pH of the emulsion (which was at 2.9) was adjusted to 5.0 by addition of ammonium hydroxide. It contained 45.8% solids. A pigment dispersion was added to the emulsion to provide a semigloss paint.

In the scrub adhesion test procedure there was employed a 6 × 17 inch black scrub test panel (=15.24 × 43.18 cm) taped to a plane plate glass panel. An alkyd enamel conforming to TT-E-489c was applied by drawdown obtaining a dry film thickness of 3 ± 0.3 mil ($\approx$0.0075 cm) and a width of 5½ inches (=13.97 cm). The enamel was allowed to dry in horizontal position for three days at 77° F ±3° F (=25° C ± 1.67° C) and at 50 ± 5% relative humidity prior to application of the test paint. The test paint was applied by drawdown in a direction perpendicular to the long axis of the panel to obtain a dry film of 2.0 ± 0.2 mils ($\approx$ 0.0051 cm) and a width of approximately 2 inches (=5.08 cm). The test paint was allowed to dry for 72 hours at the same temperature and humidity range above set out.

A cut was then made perpendicular to the long axis of the glass panel through the center of the test film, using a razor blade at a 45° angle. The panel was then placed on a Gardner Machine so that the test paint was approximately in the center of the brush stroke and was scrubbed with the brush under water, with the brush moving in a direction parallel to the long axis of the glass panel and perpendicular to the cut made in the test film. The brush was made to travel at the rate of 37 to 41 cycles per minute. To pass the test, it is required that there be no adhesion failure between the test paint and the alkyd undercoat in fewer than 5000 cycles.

As indicated above, the test paint containing the compound of formula VII showed no adhesion failure at 6000 cycles, when the test was discontinued. The control sample which did not contain this compound failed in less than 100 cycles.

EXAMPLE 5

Semigloss paints were prepared from a vinyl acetatebutyl acrylate emulsion system comprising 85.5 parts vinyl acetate to 14 parts butyl acrylate. One of said paint compositions contained 0.5 parts of the compound of formula VII and the control composition was free of such compound. The paint containing the formula VII compound tested by the above wet scrub test showed no adhesion failure at 6000 cycles while the control sample failed in less than 100 cycles.

The emulsions for the paint compositions tested were prepared as follows:

Into a jacketed reaction vessel there was charged

|  | pbw |
|---|---|
| Hydroxyethyl cellulose | 0.45 |
| Alkyl phenoxy poly (oxyethylene) ethanols | 13.7 |
| Ferrous salt | (trace) |
| De-ionized water | 318.0 |

The vessel and contents were purged with nitrogen while heated to 65° C and stirred. There were then added to the vessel at delayed intervals the three following mixtures

| Mixture 1 | pbw |
|---|---|
| Vinyl acetate | 415.2 |
| Butyl acrylate | 67.5 |
| *Pluronics | 15.6 |
| t-Butyl peroxide (70X) | 0.7 |

*Pluronics are non-ionic block polymers comprising polyoxyalkylene derivatives of propylene glycol terminating in hydroxyl.

| Mixture 2 | pbw |
|---|---|
| Sodium formaldehyde bisulfite | 0.2 |
| Sodium benzoate | 0.6 |
| De-ionized water | 8.2 |

| Mixture 3 | pbw |
|---|---|
| Compound of formula VII | 2.4 |
| De-ionized water | 72.0 |

The first and third mixtures were added over a 2 hour period while the second was added during a 15 minute period. The polymerization mixture was maintained at 65° C. After addition of the second mixture was completed, there was further added a solution of 0.6 parts of sodium formaldehyde bisulfite in 18.1 parts de-ionized water until polymerization was completed. The emulsion was then cooled to ambient temperature. It had a pH of 5.2 and contained 55.4% solids. Addition of a pigment dispersion to the emulsion provided a semigloss paint.

Similar testing was applied to aqueous paint compositions containing in the emulsion about 2% of the compound of formula VI by weight of copolymers. Compositions containing the compound of formula VI passed the test at 5000 cycles, whereas, similar compositions free of this compound failed in the test.

Another test for adhesive properties applied to water based paints and coatings is designated "floating board test." In this test, the composition to be tested is applied over a dry glossy alkyd-painted plane board surface and dried. A one-inch section of the surface is scored by cross-hatching with parallel cuts vertical and horizontal one-inch apart. An adhesive tape is applied to the dry scored surface and the relative amounts of the surface film peeled off by the adhesive observed. The board is again similarly scored and then floated face down on a water bath to wet the scored surface and the adhesive tape procedure repeated. Subjected to this test, vinyl acetate based paints containing compounds of the invention show greatly improved adherence to the alkyd surface, both wet and dry, as compared to similar paints free of these compounds.

The compounds of the invention added to polymerized vinyl acetate emulsions used in making water-based flat exterior paints also impart improved resistance to blistering.

In addition to their use as interpolymerized monomers to improve water resistance of coatings based on vinyl acetate copolymer emulsions, the monomer compounds of the present invention may be employed as such or as intermediates in resin modifiers, plasticizers, textile sizes, corrosion inhibitors, softeners for cellulosic and synthetic fabrics, antistatic agents and wet strength paper resins.

What is claimed is:

1. Compounds corresponding to the structural formula

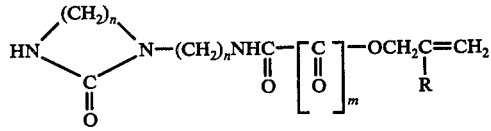

wherein $m$ is zero or one, $n$ is two or three, and R is H or $CH_3$.

2. Compounds according to claim 1 in which $n$ is 2.
3. Compounds according to claim 1 in which $m$ is 0.
4. Compounds according to claim 1 in which $m$ is 1.
5. Compounds according to claim 1 in which $n$ is 3.
6. Compounds according to claim 2 in which $m$ is 0.
7. Compounds according to claim 2 in which $m$ is 1.

8. The compound corresponding to the structural formula

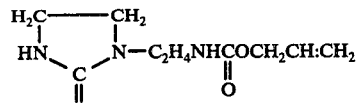

9. The compound corresponding to the structural formula

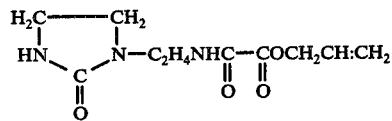

10. The method of producing compounds having the structural formula of claim 1 which comprises reacting an aminoalkyl alkylene urea with an allyl or methallyl ester of a carbonylic acid.

11. The method according to claim 10 wherein the carbonylic acid ester is allyl chloroformate.

12. The method according to claim 10 wherein the carbonylic acid ester is diallyl carbonate.

13. The method according to claim 10 wherein the carbonylic acid ester is diallyl oxalate.

14. The method according to claim 10 wherein each alkylene chain of said aminoalkyl alkylene urea has only two carbon atoms.

15. The method according to claim 14 wherein the carbonylic acid ester is allyl chloroformate.

16. The method according to claim 14 wherein the carbonylic acid ester is diallyl carbonate.

17. The method according to claim 14 wherein the carbonylic acid ester is diallyl oxalate.

18. Aqueous emulsions of vinyl ester polymer systems, the vinyl ester polymer systems comprising, as a component conferring enhanced wet adhesion properties, a reactable monomer corresponding to the structural formula of claim 1.

19. Aqueous emulsions of vinyl ester polymer systems, the vinyl ester polymer systems comprising, as a component conferring enhanced wet adhesion properties, a reactable monomer corresponding to the structural formula of claim 8.

20. Aqueous emulsions of vinyl ester polymer systems, the vinyl ester polymer systems comprising, as a component conferring enhanced wet adhesion properties, a reactable monomer corresponding to the structural formula of claim 9.

* * * * *